(12) United States Patent
Jo et al.

(10) Patent No.: US 12,391,917 B2
(45) Date of Patent: Aug. 19, 2025

(54) METHOD FOR ISOLATING STEM CELLS FROM HUMAN UMBILICAL CORD

(71) Applicant: ACESOSTEM BIOSTRATEGIES INC., Seoul (KR)

(72) Inventors: Hyun Chul Jo, Seoul (KR); Ah-Young Lee, Gyeonggi-do (KR)

(73) Assignee: ACESOSTEM BIOSTRATEGIES INC., Seoul (KR)

( * ) Notice: Subject to any disclaimer, the term of this patent is extended or adjusted under 35 U.S.C. 154(b) by 1078 days.

(21) Appl. No.: 17/040,730

(22) PCT Filed: Mar. 28, 2019

(86) PCT No.: PCT/KR2019/003674
§ 371 (c)(1),
(2) Date: Sep. 23, 2020

(87) PCT Pub. No.: WO2019/190246
PCT Pub. Date: Oct. 3, 2019

(65) Prior Publication Data
US 2021/0009944 A1 Jan. 14, 2021

(30) Foreign Application Priority Data
Mar. 29, 2018 (KR) .......................... 10-2018-0036230

(51) Int. Cl.
*C12N 5/073* (2010.01)
*A61K 35/51* (2015.01)
*C12N 5/077* (2010.01)

(52) U.S. Cl.
CPC ............ *C12N 5/0605* (2013.01); *A61K 35/51* (2013.01); *C12N 5/0653* (2013.01); *C12N 5/0654* (2013.01); *C12N 5/0655* (2013.01); *C12N 5/066* (2013.01); *C12N 2506/025* (2013.01)

(58) Field of Classification Search
CPC ............ C12N 5/0605; C12N 2506/025; C12N 2509/10; A61K 35/51
See application file for complete search history.

(56) References Cited

FOREIGN PATENT DOCUMENTS

| CN | 102220338 | 10/2011 | |
|---|---|---|---|
| CN | 104232574 | 12/2014 | |
| CN | 105420179 | 3/2016 | |
| KR | 1020080081053 | 9/2008 | |
| KR | 1020090008784 | 1/2009 | |
| KR | 1020110134253 | 12/2011 | |
| KR | 1020150016117 | 2/2015 | |
| KR | 1020170108325 | 9/2017 | |
| WO | WO-2018067071 A1 * | 4/2018 | ............ A61K 35/28 |

OTHER PUBLICATIONS

Filiz et al., Positive correlation between the quantity of Wharton's jelly in the umbilical cord and birth weight, Taiwanese Journal of Obstetrics & Gynecology 50 (2011) pp. 33-36 (Year: 2011).*

Mori et al., Improved Explant Method to Isolate Umbilical Cord-Derived Mesenchymal Stem Cells and Their Immunosuppressive Properties, Tissue Engineering Part C: Methods. Apr.367-372. (Year: 2015).*

Capelli, Chiara, et al. "Minimally manipulated whole human umbilical cord is a rich source of clinical-grade human mesenchymal stromal cells expanded in human platelet lysate." Cytotherapy 13.7 (2011): 786-801. (Year: 2011).*

Filiz, Avsar A., et al. "Positive correlation between the quantity of Wharton's jelly in the umbilical cord and birth weight." Taiwanese Journal of Obstetrics and Gynecology 50.1 (2011): 33-36. (Year: 2011).*

Ryu, Hak-Hyun, et al. "Comparison of mesenchymal stem cells derived from fat, bone marrow, Wharton's jelly, and umbilical cord blood for treating spinal cord injuries in dogs." Journal of Veterinary Medical Science 74.12 (2012): 1617-1630. (Year: 2012).*

Mori, Yuka, et al. "Improved explant method to isolate umbilical cord-derived mesenchymal stem cells and their immunosuppressive properties." Tissue Engineering Part C: Methods 21.4 (2015): 367-372. (Year: 2015).*

Egger, D.; Tripisciano, C.; Weber, V.; Dominici, M.; Kasper, C. Dynamic Cultivation of Mesenchymal Stem Cell Aggregates. Bioengineering 2018, 5, 48. (Year: 2018).*

Paladino, F.V., et al., "Comparison between isolation protocols highlights intrinsic variability of human umbilical cord mesenchymal cells," Cell Tissue Bank, 2016, 17, 123-136.

Hassan, G., et al., "A Simple Method to Isolate and Expand Human Umbilical Cord Derived Mesenchymal Stem Cells: Using Explant Method and Umbilical Cord Blood Serum," International Journal of Stem Cells, 2017, vol. 10, No. 2, pp. 184-192.

Mennan, C., et al., "Isolation and Characterisation of Mesenchymal Stem Cells from Different Regions of the Human Umbilical Cord," BioMed Research International, 2013, vol. 2013, Article ID 916136, 8 pages.

Lee, H.R., et al., "Cryopreservation of Umbilical Cord as a Source of Mesenchymal Stromal Cells and Growth Factors," Korean J Blood Transfus. Aug. 2012;23(2):115-126.

Hua, J., et al., "Comparison of different methods for the isolation of mesenchymal stem cells from umbilical cord matrix: Proliferation and multilineage differentiation as compared to mesenchymal stem cells from umbilical cord blood and bone marrow," Cell Biol Int 38 (2014) 198-210.

(Continued)

*Primary Examiner* — Maria G Leavitt
*Assistant Examiner* — Michael Angelo Riga
(74) *Attorney, Agent, or Firm* — Gregory M. Lefkowitz; Brandon A. Chan

(57) ABSTRACT

The present invention relates to a method for isolating umbilical cord-derived stem cells, and more specifically to a method for isolating a significantly large number of mesenchymal stem cells from the umbilical cord having a specified size. The method of the present invention has a great advantage in that since stem cells can be isolated from an umbilical cord tissue without enzymatic treatment, stress applied to the cells can be significantly suppressed. In addition, stem cells obtained by the method of the present invention have superior proliferative capacity compared to stem cells obtained by conventional isolation methods.

4 Claims, 9 Drawing Sheets

(56) References Cited

OTHER PUBLICATIONS

Montanucci, P., et al., "New Simple and Rapid Method for Purification of Mesenchymal Stem Cells from the Human Umbilical Cord Wharton Jelly," Tissue Eng Part A. Nov. 2011;17(21-22):2651-61.

Kim, S.M., et al., "Alternative xeno-free biomaterials derived from human umbilical cord for the self-renewal ex-vivo expansion of mesenchymal stem cells," Stem Cells Dev. Nov. 15, 2013;22(22):3025-38.

Yan, M., et al., "Conversion of human umbilical cord mesenchymal stem cells in Wharton's jelly to dopamine neurons mediated by the Lmx1a and neurturin in vitro: potential therapeutic application for Parkinson's disease in a rhesus monkey model," PLoS One. May 28, 2013;8(5):e64000.

Chatzistamatiou, T.K., et al., "Optimizing isolation culture and freezing methods to preserve Wharton's jelly's mesenchymal stem cell (MSC) properties: an MSC banking protocol validation for the Hellenic Cord Blood Bank," Transfusion. Dec. 2014;54(12):3108-20.

Yoon, J.H., et al., "Comparison of explant-derived and enzymatic digestion-derived MSCs and the growth factors from Wharton's jelly," Biomed Res Int. 2013;2013:428726.

Jo, C.H., et al., "Fetal mesenchymal stem cells derived from human umbilical cord sustain primitive characteristics during extensive expansion," Cell Tissue Res. Dec. 2008;334(3):423-33.

* cited by examiner

METHOD FOR ISOLATING STEM CELLS FROM HUMAN UMBILICAL CORD

CROSS-REFERENCE TO RELATED APPLICATIONS

This application is a § 371 national stage entry of International Application No. PCT/KR2019/003674, filed on Mar. 28, 2019, which claims priority to South Korean Patent Application No. 10-2018-0036230, filed on Mar. 29, 2018, the entire contents of which are incorporated herein by reference.

TECHNICAL FIELD

The present invention relates to a method for isolating umbilical cord-derived stem cells, and more specifically to a method for isolating a significantly large number of mesenchymal stem cells from the umbilical cord having a specified size.

BACKGROUND ART

Stem cells are cells that can differentiate into a variety of cells constituting biological tissues. Stem cells refer collectively to undifferentiated cells that can be obtained from embryonic, fetal, and adult tissues. In terms of their capacity for differentiation, stem cells can be classified as pluripotent, multipotent, and unipotent stem cells. Pluripotent stem cells have the potential to differentiate into all types of cells and include embryonic stem cells (ES cells) and induced pluripotent stem cells (iPS cells). Multipotent and/or unipotent stem cells may be, for example, adult stem cells such as hematopoietic stem cells, mesenchymal stem cells, and neural stem cells.

The utilization of stem cells is thought as a new alternative in the treatment of incurable diseases (Korean Patent Publication No. 2015-0016117). Organ transplantation and gene therapy have been proposed so far for the treatment of incurable diseases but their efficient practical application is still limited due to immune rejection, a shortage of organs or a lack of knowledge about vector development and disease genes.

Under such circumstances, there has been an ever-increasing interest in research on stem cells and various possibilities have been proposed for the use of stem cells to regenerate organs and treat Parkinson's disease, diabetes, and spinal cord injury.

Several approaches exist for securing stem cell sources. iPS cells have recently proposed new possibilities to secure adult stem cells without ethical problems but they are still in the very early stages of research and need to be scientifically verified for practical alternatives.

Techniques for utilizing adult stem cell sources such as bone marrow and adipose have emerged as solutions to the above-mentioned problems. However, stem cells hardly differentiate to a certain extent and particularly continuous passages of bone marrow- and adipose-derived mesenchymal stem cells lead to rapid aging of the stem cells. Further, aged bone marrow stem cells per se are difficult to subculture. In other words, stem cells from the elderly or patients with chronic diseases deteriorate in quality.

Specifically, it was found that stem cells taken from aged donors have poor ability to form colonies, low proliferation rate, and poor differentiation potential and stem cells taken from patients with chronic diseases such as osteoarthritis have decreased proliferative capacity and differentiation potential compared to those from normal groups.

Patients complain of discomfort when their stem cells are taken and most of the stem cells cannot also be used due to their low quality. For transplantation of or treatment with allogeneic mesenchymal stem cells, the supply of a sufficient amount of the stem cells with high quality is urgently needed to ensure rapid use of the stem cells and determine the suitability for transplantation of the stem cells, for example, by testing infectious markers necessary for transplantation. That is, conventional techniques are limited in providing a sufficient amount of stem cells because they have limitations in isolating and culturing stem cells.

Biological wastes discarded after childbirth are composed of the youngest cells and are sources of adult stem cells. Such biological waste tissues include umbilical cord blood, umbilical cord, placenta, and amnion. Particularly, umbilical cord blood is already recognized as a source of hematopoietic stem cells for therapeutic applications. However, since umbilical cord blood-derived mesenchymal stem cells suffer from very low success rate of isolation, many problems may be caused when mesenchymal stem cells are not isolated from umbilical cord blood after storage. Hows et al. and Wexler et al. reported that mesenchymal stem cells cannot be isolated from umbilical cord blood (Hows, 1992; Wexler, 2003; Pojda, 2005; Bieback, 2004). As such, the success rate of isolation of mesenchymal stem cells from umbilical cord blood is not very high.

Umbilical cord tissues have emerged as new sources for cell therapy. The umbilical cord is a fetal tissue and is thus the youngest tissue from which stem cells other than embryos can be taken. Accordingly, the use of the umbilical cord can basically prevent the quality of stem cells from deterioration resulting from age and various diseases and thus has a fundamental advantage in that the shortcomings of embryonic and adult stem cells can be avoided. In particular, umbilical cord-derived stem cells were reported to form a larger number of CFU-Fs, proliferate faster, and can be passaged more times than bone marrow-derived stem cells (Karahuseyinoglu, 2007; Lund, 2007; Baksh, 2007; Lu, 2006).

Thus, there arises a need to develop a technique for isolating a large number of stem cells from the umbilical cord while maintaining their activity as much as possible.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The present inventors have earnestly and intensively conducted research to develop a method for producing a large amount of stem cells from an umbilical cord tissue. As a result, the present inventors have designed a strategy for isolating a large number of stem cells with high proliferative capacity and have found based on this strategy that when an umbilical cord tissue is explanted and cultured, stem cells can be produced on a large scale. The present invention has been accomplished based on this finding.

Therefore, one object of the present invention is to provide a method for isolating umbilical cord-derived stem cells.

A further object of the present invention is to provide umbilical cord-derived stem cells obtained by the method.

Another object of the present invention is to provide a cell therapeutic agent including the umbilical cord-derived stem cells or their differentiated cells as active ingredients.

Still another object of the present invention is to provide a pharmaceutical composition including the umbilical cord-derived stem cells or their differentiated cells as active ingredients.

Other objects and advantages of the invention become more apparent from the following detailed description, claims, and drawings.

Means for Solving the Problems

One aspect of the present invention provides a method for isolating umbilical cord-derived stem cells including (a) grinding an isolated umbilical cord tissue into explants having a width of 2 to 4 mm and a length of 2 to 4 mm and (b) culturing the explants in a culture medium.

The culture medium may be added in an amount of 0.5 to 3.0 ml per gram of the umbilical cord tissue.

The culture medium may be selected from the group consisting of Dulbecco's minimum essential medium (DMEM), RPMI, Ham's F-10, Ham's F-12, α-minimal essential medium (α-MEM), Glasgow's minimal essential medium (GMEM), Iscove's modified Dulbecco's medium (IMDM), and combinations thereof.

The explants may be cultured to reach 0.0007 to 0.0068 g per unit area ($cm^2$).

Step (b) may be carried out for 60 to 120 minutes.

A further aspect of the present invention provides umbilical cord-derived stem cells obtained by the method.

Another aspect of the present invention provides a cell therapeutic agent including the umbilical cord-derived stem cells or their differentiated cells as active ingredients.

The differentiated cells may be selected from the group consisting of mesoderm-derived cells, endoderm-derived cells, ectoderm-derived cells, and combinations thereof.

The differentiated cells may be selected from the group consisting of neurons, oligodendrocytes, astrocytes, Schwann cells, osteoblasts, chondrocytes, adipocytes, tenocytes/ligamentocytes, myocytes, and combinations thereof.

The cell therapeutic agent may further include one or more ingredients selected from the group consisting of protein and peptide preparations, glycosaminoglycans, proteoglycans, growth factors, and gene therapy agents.

The cell therapeutic agent may further include one or more ingredients selected from the group consisting of anti-inflammatory drugs, stem cell recruitment factors, and vascular growth factors.

The cell therapeutic agent may be provided in the form of an injectable preparation including the umbilical cord-derived stem cells or their differentiated cells as active ingredients or may be loaded on a support or carrier.

Yet another aspect of the present invention provides a pharmaceutical composition including the umbilical cord-derived stem cells or their differentiated cells as active ingredients.

The pharmaceutical composition may be used to prevent or treat a bone, cartilage, muscular, tendon or ligament disease.

The pharmaceutical composition may be used to prevent or treat an osseous metabolic disease.

The osseous metabolic disease may be osteoporosis, Paget's disease, periodontal disease, bone metastatic cancer or rheumatoid arthritis.

Effects of the Invention

The features and advantages of the present invention are summarized as follows:
(i) The method of the present invention is efficient in isolating stem cells from the umbilical cord.
(ii) The method of the present invention can be used to isolate a significantly large number of stem cells from the umbilical cord of the same size compared to the use of conventional methods.
(iii) The method of the present invention has a great advantage in that since stem cells can be isolated from an umbilical cord tissue without enzymatic treatment, stress applied to the cells can be significantly suppressed. In addition, stem cells obtained by the method of the present invention have superior proliferative capacity compared to stem cells obtained by conventional isolation methods.

That is, the method of the present invention enables simple and efficient isolation of a large number of stem cells from the umbilical cord having a specified size by explantation, thus being suitable for use in applications where a large amount of stem cells is required or in therapeutic applications.

BEST MODE FOR CARRYING OUT THE INVENTION

Figure 1A:
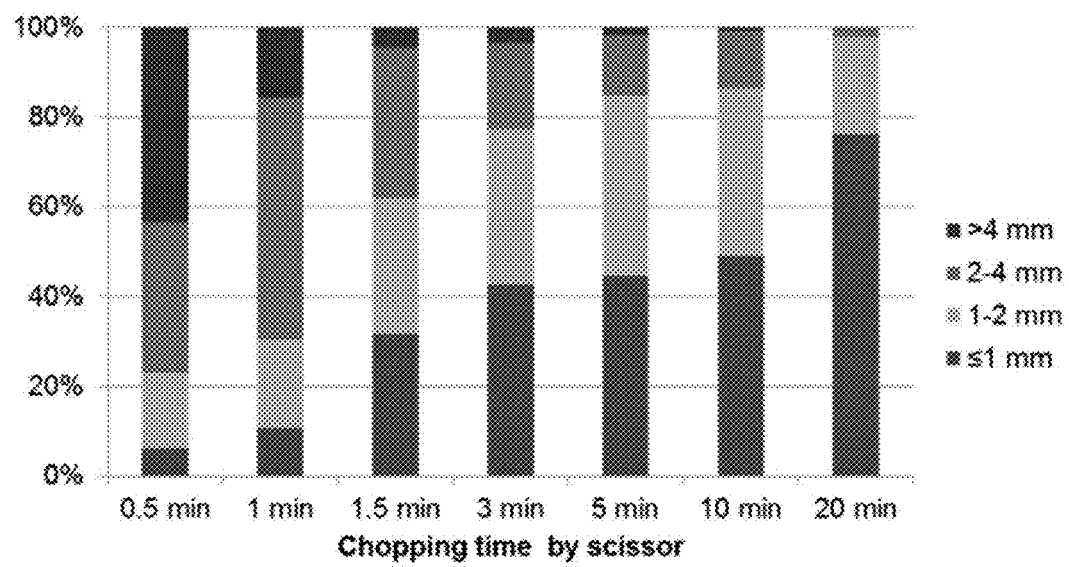
FIG. 1A shows changes in the number of tissue explants prepared as a function of chopping time in Examples 1-5.

One aspect of the present invention provides a method for isolating umbilical cord-derived stem cells.

Embryonic stem cells have ethical problems. Induced pluripotent stem cells offer new possibilities but are still in early stages of research. Thus, induced pluripotent stem cells need to be scientifically verified for practical alternatives. Bone marrow and adipose stem cells are currently in the spotlight as adult stem cells but have problems in that their frequency, proliferative capacity, and differentiation potential decrease with age. Another problem of bone marrow and adipose stem cells is that invasive treatment is required to obtain tissues from which the stem cells are isolated.

As a result of investigation to overcome these limitations and problems, the present inventors have found that stem cells with enhanced in vitro proliferative capacity and remarkable differentiation potential can be obtained in high yield without enzymatic or additional processing from explants having a specified size from the umbilical cord. The present invention has been accomplished based on this finding.

As used herein, the term "umbilical cord" refers to the cord connecting the placenta to the fetus.

As used herein, the term "umbilical cord-derived stem cells" refers to stem cells isolated from the umbilical cord and their associated tissues, preferably umbilical cord blood, umbilical cord vein subendothelium, umbilical cord perivascular matrix, umbilical cord Wharton's Jelly, umbilical cord subamnion and amnion, amniotic fluid, placenta, and chorion. The umbilical cord-derived stem cells are more preferably those isolated from umbilical cord blood, umbilical cord vein subendothelium, umbilical cord perivascular matrix, umbilical cord Wharton's Jelly or umbilical cord subamnion.

In particular, the umbilical cord is likely to be readily available without special operation or medical treatment during parturition because it is discarded after parturition, unlike other organs and tissues. The umbilical cord is known to contain a large number of stem cells for its amount. Various requirements need to be met for in vitro culture of stem cells from the umbilical cord. Even when cultured, only a very small amount of stem cells are collected, limiting their use for the development of therapeutic agents.

Specifically, the method includes (a) grinding an isolated umbilical cord tissue into explants having a width of 2 to 4 mm and a length of 2 to 4 mm and (b) culturing the explants in a culture medium.

According to a preferred embodiment of the present invention, the method further includes (c) collecting umbilical cord-derived stem cells after culture.

The umbilical cord is a representative tissue from which stem cells can be derived. Since the umbilical cord can be taken without involving special operation or medical treatment and with no side effects during parturition, there is no problem in terms of demand and supply for the tissue from which stem cells are isolated and cultured. In addition, the umbilical cord is less likely to be contaminated with heterogeneous cells, thus being advantageous in the isolation and culture of stem cells to prepare therapeutic agents for incurable diseases.

As described above, however, umbilical cord-derived stem cells are very troublesome and difficult to culture in vitro. Even though cultured, only a very small number of umbilical cord-derived stem cells are collected due to their considerably low yield or the differentiation potential of umbilical cord-derived stem cells is very poor.

Therefore, the method of the present invention intends to collect a large amount of stem cells and isolate stem cells with enhanced differentiation potential.

First, an isolated umbilical cord tissue is ground into explants having a width of 2 to 4 mm and a length of 2 to 4 mm (step (a)). 30% or more, preferably 50% or more, more preferably 70% or more of the ground explants from the isolated umbilical cord tissue have a width of 2 to 4 mm and a length of 2 to 4 mm. Most preferably, 50% to 70% of the explants have a width of 2 to 4 mm and a length of 2 to 4 mm. The tissue may be chopped into hexahedral explants having a width of 2 to 4 mm, a length of 2 to 4 mm, and a height of 2 to 4 mm. The uniform size of the explants results in a significant increase in the number of cells to be isolated from the explants. This can be seen from the following experimental examples. For isolation of umbilical cord-derived stem cells, step (a) may include introducing an umbilical cord tissue into a culture medium and chopping the umbilical cord tissue into explants having a width of 2 to 4 mm and a length of 2 to 4 mm. This introduction facilitates the preparation of uniformly sized explants and enables the chopping of a small amount of the tissue into uniformly sized explants with minimal scissoring, which decreases the possibility of contamination and thus makes it easy to isolate and culture stem cells in the subsequent step.

A culture medium is added in an amount of 0 to 10 ml, preferably 0 to 5.0 ml, more preferably 0.5 to 3.0 ml per gram of the umbilical cord tissue. If the amount of the culture medium per gram of the umbilical cord tissue exceeds 10.0 ml, a reduced number of cells may be isolated.

Subsequently, the explants are cultured in the culture medium (step (b)). The explants are cultured to reach 0.0001 to 0.05 g, preferably 0.0006 to 0.03 g, more preferably 0.0006 to 0.0135 g, most preferably 0.0007 to 0.0068 g per unit area ($cm^2$) of a culture dish. The presence of the explants in an amount of less than 0.0001 g or exceeding 0.05 g per unit area ($cm^2$) of the culture dish may significantly reduce the number of cells to be isolated.

Step (b) is preferably carried out for 1 to 600 minutes, preferably 10 to 180 minutes, more preferably 30 to 120 minutes, most preferably 60 to 120 minutes. Culture of the explants for less than 1 minute or more than 600 minutes may significantly reduce the number of cells to be isolated.

When all of the above-described culture conditions are met, $1 \times 10^6$ to $5 \times 10^6$, preferably $1.5 \times 10^6$ to $2 \times 10^6$ cells can be isolated from 1 g of the explants. This demonstrates that the method of the present invention is advantageous over conventional methods, as shown in Table 1.

TABLE 1

| Isolation method | Number of cells isolated from 1 g of explants |
| --- | --- |
| The inventive method satisfying all conditions | 1,820,000 ± 44,000 |

TABLE 1-continued

| Isolation method | Number of cells isolated from 1 g of explants |
|---|---|
| Hua, 2014[1] | 67,000 ± |
| Montanucci, 2011[2] | 300,000 ± |
| Kim, 2013[3] | 130,000 ± 20,000 |
| Yan, 2013[4] | 150,000 ± |
| Chatzistamatiou, 2014[5] | 302,000 ± 66,000 |
| Yoon, 2013[6] | 489,000 ± 320,000 |
| Jo, 2008[7] | 399,000 ± 522,000 |

[1] Hua J, Gong J, Meng H, et al. Comparison of different methods for the isolation of mesenchymal stem cells from umbilical cord matrix: Proliferation and multilineage differentiation as compared to mesenchymal stem cells from umbilical cord blood and bone marrow. Cell Biology International. 2014; 38(2): 198-210.
[2] Montanucci P, Basta G, Pescara T, Pennoni I, Di Giovanni F, Calafiore R. New simple and rapid method for purification of mesenchymal stem cells from the human umbilical cord Wharton jelly. Tissue Eng Part A. 2011; 17(21-22): 2651-2661.
[3] Kim S M, Moon S H, Lee Y, Kim G J, Chung H M, Choi Y S. Alternative xeno-free biomaterials derived from human umbilical cord for the self-renewal ex-vivo expansion of mesenchymal stem cells. Stem Cells Dev. 2013; 22(22): 3025-3038.
[4] Yan M, Sun M, Zhou Y, et al. Conversion of human umbilical cord mesenchymal stem cells in Wharton's jelly to dopamine neurons mediated by the Lmx1a and neurturin in vitro: potential therapeutic application for Parkinson's disease in a rhesus monkey model. PLoS One. 2013; 8(5): e64000.
[5] Chatzistamatiou T K, Papassavas A C, Michalopoulos E, et al. Optimizing isolation culture and freezing methods to preserve Wharton's jelly's mesenchymal stem cell (MSC) properties: an MSC banking protocol validation for the Hellenic Cord Blood Bank. Transfusion. 2014; 54(12): 3108-3120.
[6] Yoon J H, Roh E Y, Shin S, et al. Comparison of explant-derived and enzymatic digestion-derived MSCs and the growth factors from Wharton's jelly. Biomed Res Int. 2013; 2013: 428726.
[7] Jo C H, Kim O S, Park E Y, et al. Fetal mesenchymal stem cells derived from human umbilical cord sustain primitive characteristics during extensive expansion. Cell Tissue Res. 2008; 334(3): 423-433.

The culture medium may mean a medium where the activity of umbilical cord-derived stem cells can be maintained in vitro or the proliferation of umbilical cord-derived stem cells can be induced. The culture medium may be any of those that are commonly used for culturing mammalian cells. Examples of commercially available products for the culture medium include Dulbecco's minimum essential medium (DMEM), RPMI, Ham's F-10, Ham's F-12, α-minimal essential medium (α-MEM), Glasgow's minimal essential medium (GMEM), and Iscove's modified Dulbecco's medium (IMDM).

The culture medium may further include serum (i.e. serum of animals, including human beings) and/or one or more growth factors that can promote the proliferation of umbilical cord-derived stem cells. Examples of these growth factors include, but are not limited to, basic fibroblastic growth factor (bFGF), vascular endothelial growth factor (VEGF), insulin, epidermal growth factor (EGF), leukemia inhibitory factor (LIF), insulin-like growth factor (IGF), platelet-derived growth factor (PDGF), platelet-rich plasma (PRP), platelet lysate (PL), and stem cell factor (SCF).

The growth culture medium may include one or more antibiotics such as penicillin, streptomycin, and gentamicin.

The culture medium may be composed of DMEM:Ham's F12 (1:1), fetal bovine serum, EGF, bFGF, IGF, and gentamicin. More specifically, the culture medium may be composed of 70 to 95% (vol/vol) DMEM:Ham's F12 (1:1), 5 to 15% (vol/vol) fetal bovine serum, 5 to 50 ng/ml EGF, 0.5 to 10 ng/ml bFGF, 5 to 50 ng/ml IGF, and 5 to 50 mg/ml gentamicin.

After culture, umbilical cord-derived stem cells are collected. The collected umbilical cord-derived stem cells can be amplified. There is no particular restriction on the amplification method, but the amplification is preferably performed by monolayer culture. The collected umbilical cord-derived stem cells are seeded in a culture dish. Thereafter, when the stem cells are cultured to cover 60 to 90% of the surface area of the culture dish, they are detached from the culture dish by treatment with trypsin-EDTA and are again seeded in a new culture dish. This passage can be repeated to amplify the cells such that the cells are provided as many as needed for a therapeutic dose.

The method of the present invention enables unlimited repeated culture of umbilical cord-derived stem cells from a small amount of the umbilical cord so that the stem cells can be isolated as many as necessary to treat incurable diseases without repeated sampling of the umbilical cord tissue.

The umbilical cord-derived stem cells are mesenchymal stem cells that can be differentiated into endoderm, mesoderm, ectoderm, and tissues and tissue cells derived therefrom.

According to a preferred embodiment of the present invention, the mesoderm-derived cells are selected from the group consisting of osteoblasts, chondrocytes, adipocytes, skeletal muscle cells, and combinations thereof.

According to one embodiment of the present invention, the umbilical cord-derived stem cells have adipogenic, osteogenic, chondrogenic, and tendo/ligamentogenic differentiation potentials.

The umbilical cord-derived stem cells have a doubling time of 30-50 hours, indicating their superior in vitro growth capacity. The doubling time refers to the time it takes for one cell to divide into two cells. The umbilical cord-derived stem cells have better in vitro growth capacity than mesenchymal stem cells, whose doubling time is 60 hours, obtained by conventional culture methods. Therefore, the method of the present invention can ensure an effective dose of stem cells necessary for the treatment of incurable diseases in a short time.

The umbilical cord-derived stem cells may be mesenchymal stem cells that can be differentiated into various cell types. Examples of such cell types include, but are not limited to, neurons, oligodendrocytes, astrocytes, Schwann cells, osteoblasts, chondrocytes, adipocytes, tenocytes/ligamentocytes, and myocytes.

The cell types into which the umbilical cord-derived stem cells can be spontaneously differentiated are not particularly limited, but are preferably osteoblasts, chondrocytes, adipocytes, tenocytes/ligamentocytes, and myocytes.

A further aspect of the present invention provides umbilical cord-derived stem cells obtained by the method.

Another aspect of the present invention provides a cell therapeutic agent including umbilical cord-derived stem cells obtained by the method or their differentiated cells as active ingredients.

The cell therapeutic agent can directly use the umbilical cord-derived stem cells without involving a special differentiation process. Alternatively, the cell therapeutic agent may use cells into which the umbilical cord-derived stem cells are differentiated for targeted cell therapy.

The differentiated cells used in the cell therapeutic agent are not particularly limited and may be, for example, selected from the group consisting of neurons, oligodendrocytes, astrocytes, Schwann cells, osteoblasts, chondrocytes, adipocytes, tenocytes/ligamentocytes, myocytes, and combinations thereof.

According to a preferred embodiment of the present invention, the cell therapeutic agent may further include one or more ingredients selected from the group consisting of protein and peptide preparations, glycosaminoglycans, proteoglycans, growth factors, and gene therapy agents.

The cell therapeutic agent of the present invention may further have benefit from the paracrine effects of MSC-derived extracellular vesicles, including miRNA-containing exosomes and microvesicles secreted by the stem cells, and a matrix, in addition to the effects resulting from differentiation of the stem cells into endoderm, mesoderm, and ectoderm. The paracrine effects of the stem cells are well known in the art (Korean Patent Publication No. 2017-0103697 (Treatment of hepatic fibrosis), U.S. Patent Publication No. 2015-0190429 (Anti-inflammatory and immune suppressive effects), European Patent Publication No. 3145493 (Treatment of lung disease), and Chinese Patent Publication No. 101854941 (Treatment of acute renal failure)).

There is no particular restriction on the use of the umbilical cord-derived stem cells or their differentiated cells in the cell therapeutic agent. The umbilical cord-derived stem cells or their differentiated cells can be used by any suitable method known in the art. The umbilical cord-derived stem cells are preferably loaded on a support or carrier.

The support or carrier may be one that does not cause any substantially harmful response to a host and is optionally biodegradable or can be naturally removed from and/or chemically incorporated into a biological system. The support or carrier is not limited to a particular kind but is preferably in the form of a gel or hydrogel containing fibrin, platelet lysate, platelet rich plasma (PRP) or a natural or synthetic polymer.

The umbilical cord-derived stem cells may be used in admixture with a hydrogel. The hydrogel material is not particularly limited but is a natural polymer, preferably a collagen hydrogel. The in vivo degradation rate of the collagen hydrogel can be controlled by varying the collagen concentration. The use of the hydrogel can prevent the cells from being lost through blood when the cells are injected and can reduce damage to the cells caused by inflammatory cells and enzymes at injury sites.

The cell therapeutic agent may further include one or more ingredients selected from the group consisting of anti-inflammatory drugs, stem cell recruitment factors, and vascular growth factors.

The anti-inflammatory drugs serve to protect the umbilical cord-derived stem cells transplanted with the hydrogel from excessive inflammatory responses. The stem cell recruitment factors and the vascular growth factors serve to induce the recruitment of the stem cells and vascular growth in peripheral nerves, respectively, achieving enhanced cell regeneration.

Examples of the anti-inflammatory drugs include, but are not particularly limited to, COX inhibitors, ACE inhibitors, salicylates, steroids and anabolic steroids, including dexamethasone and testosterone, and precursors thereof.

Examples of the stem cell recruitment factors include, but are not particularly limited to, IGF, bFGF, PDGF, and EGF.

The vascular growth factors include, but are not particularly limited to, EGF, PDGF, VEGF, ECGF, and angiogenin.

According to a preferred embodiment of the present invention, the cell therapeutic agent may be used in combination with one or more ingredients selected from the group consisting of protein and peptide preparations, glycosaminoglycans, proteoglycans, growth factors, and gene therapy agents.

The cell therapeutic agent of the present invention may be provided in the form of an injectable preparation including the umbilical cord-derived stem cells or their differentiated cells as active ingredients or may be loaded on a support or carrier.

Yet another aspect of the present invention provides a pharmaceutical composition including the umbilical cord-derived stem cells or their differentiated cells as active ingredients.

The pharmaceutical composition of the present invention benefits from the ability of the stem cells to regenerate tissue, has a prophylactic or therapeutic effect on diseases based on the tissue regeneration ability, and exhibits anti-inflammatory and immunomodulatory effects resulting from the paracrine action of the stem cells.

Based on its ability to regenerate tissue and its prophylactic or therapeutic effect on diseases, the pharmaceutical composition of the present invention can be used to prevent or treat various diseases, including but not limited to, 1) damage to heart, blood, and blood vessel and diseases caused thereby in the circulatory system, 2) damage to skin, hair, fat, and nail and diseases caused thereby in the integumentary system, 3) damage to bone, cartilage, tendon, ligament, and muscle and diseases caused thereby in the skeletal system, 4) damage to genitals such as ovary, fallopian tube, uterus, vagina, mammary gland, testicle, seminal duct, semen, and prostate and diseases caused thereby in the reproductive system, 5) damage to salivary gland, esophagus, stomach, liver, gallbladder, pancreas, intestine, rectum, and anus and diseases caused thereby in the digestive system, 6) damage to body fluid, electrolyte balance, kidney, ureter, bladder, and urethra and diseases caused thereby in the urinary system, 7) damage to trachea, pharynx, larynx, bronchi, lung, and diaphragm and diseases caused thereby in the respiratory system, 8) damage to hypothalamus, pituitary gland, pineal body or pineal gland, thyroid gland, parathyroid gland, adrenal gland, and endocrine gland and diseases caused thereby in the endocrine system, 9) damage to the immune system and diseases caused thereby, 10) damage to lymph node and blood vessel and diseases caused thereby in the lymphatic system, 11) damage to skeletal muscle, smooth muscle, and cardiac muscle and diseases caused thereby in the muscular system, and 12) damage to brain, spinal cord, autonomic nerve, and peripheral nerve and diseases caused thereby in the nervous system.

Based on its anti-inflammatory and immunomodulatory effects, the pharmaceutical composition of the present invention can be used to treat various diseases, including but not limited to, 1) joint diseases, including arthritis, Behcet's disease, and gout, and inflammatory diseases in various organs and tissues, 2) autoimmune diseases, including lupus, atopy, and rheumatoid arthritis, 3) tumors, including cancers, 4) infectious diseases and shock, 5) adverse reactions and GVHD after transplantation.

According to a preferred embodiment of the present invention, the pharmaceutical composition is used to prevent or treat a bone, cartilage, muscle, tendon or ligament disease.

The pharmaceutical composition of the present invention may also be used to prevent or treat an osseous metabolic disease. Preferably, the pharmaceutical composition of the present invention is used for the purpose of preventing or treating osteoporosis, Paget's disease, periodontal disease, bone metastasis cancer or rheumatoid arthritis.

The method of the present invention enables the culture of a large amount of umbilical cord-derived stem cells within 60 to 120 minutes. In addition, according to the method of the present invention, an effective amount of umbilical cord-derived stem cells having a PDT of 30 to 50 hours, indicating their superior in vitro growth capacity, and suitable for use in a cell therapeutic agent can be acquired in a short time.

The superior in vitro proliferative capacity and multipotency of the umbilical cord-derived stem cells according to the present invention allow the pharmaceutical composition to benefit from the ability to regenerate tissue, have a prophylactic or therapeutic effect on diseases based on the tissue regeneration ability, and/or exhibit anti-inflammatory and immunomodulatory effects.

The pharmaceutical composition of the present invention includes one or more pharmaceutically acceptable carriers that are commonly used for formulation. Examples of these pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. The pharmaceutical composition of the present invention may further include at least one additive selected from the group consisting of lubricating agents, wetting agents, sweetening agents, flavoring agents, emulsifying agents, suspending agents, and preservatives. Details of suitable pharmaceutically acceptable carriers and formulations can be found in *Remington's Pharmaceutical Sciences* (19th ed., 1995).

The pharmaceutical composition of the present invention can be administered orally or parenterally, preferably parenterally. For example, the pharmaceutical composition of the present invention may be injected intravenously, topically or intraperitoneally.

A suitable dosage of the pharmaceutical compositions according to the present invention may vary depending on various factors such as formulation method, mode of administration, patient's age, body weight, sex, and pathological condition, diet, time and route of administration, rate of excretion, and responsiveness. A physician having ordinary skill in the art can readily determine and prescribe a desired therapeutically or prophylactically effective amount of the pharmaceutical composition.

The pharmaceutical composition of the present invention can be prepared in unit dosage forms or dispensed in multi-dose containers with a pharmaceutically acceptable carrier and/or excipient by a suitable method which can be easily carried out by one having ordinary skill in the art. The pharmaceutical composition of the present invention may be provided in the form of an injectable formulation including the umbilical cord-derived stem cells or their differentiated cells as active ingredients or may be loaded on a support or carrier. The pharmaceutical composition of the present invention may be optionally used in combination with one or more other substances selected from the group consisting of protein and peptide preparations, glycosaminoglycans, proteoglycans, growth factors, and gene therapy agents.

MODE FOR CARRYING OUT THE INVENTION

The present invention will be explained in more detail with reference to the following examples. It will be evident to those skilled in the art that the scope of the present invention is not limited by these examples according to the gist of the present invention.

Experimental Methods

1. Colony-Forming Unit-Fibroblast (CFU-F) Assay

On day 14 of culture, a culture dish was washed twice with DPBS and cells were fixed in 4% paraformaldehyde for 20 min and stained with 0.1% crystal violet solution (Merck, Darmstadt, Germany) for 10 min. A cell aggregate consisting of ≥50 stained cells was defined as a CFU-F. The number and area of the CFU-Fs were measured.

2. Assay for Proliferative Capacity of Stem Cells (Growth Kinetics Assay)

The proliferative capacity of stem cells was analyzed by measuring the cumulative population doubling level (CPDL) and population doubling time (PDT) of the stem cells. Stem cells were passaged nine times for a total culture period of 60 days, including the time required to isolate the stem cells. The cumulative population doubling level was measured by inoculating umbilical cord-derived stem cells at a density of 3,333 cells/cm$^2$ into a culture dish and measuring the number of cells at each passage by trypan blue exclusion. The population doubling time (PDT) was calculated by PD=Log (Nf/Ni)/Log 2 and PDT=CT/PD (where Ni is the initial cell number and Nf is the final cell number. Each experiment was repeated three times.

3. Immunophenotyping

The immunophenotypes of cell surface antigens was analyzed using cells after the third passage (P3) by flow cytometry. Cells were washed with DPBS, plated at a density of 2×10$^5$, and centrifuged and a cold staining buffer (DPBS, 0.1% sodium azide, and 2% fetal bovine serum) was added thereto.

A total of eight antibodies conjugated with fluorescein isothiocyanate (FITC) or phycoerythrin (PE) were allowed to react in a darkroom at 4° C. for 30 min. The antibodies were HLA-DR, CD11b, CD19, CD34, CD45, CD73, CD90 (all of which are available from Becton Dickinson, San Jose, Calif., USA), and CD105 (available from Abcam, Cambridge, UK). Then, cells were washed with DPBS and fixed in 1% paraformaldehyde. IgG1-FITC, IgG1-PE, and IgG2a-FITC (all of which are available from Becton Dickinson, San Jose, Calif., USA) were used as isotypic controls. Data were analyzed with Becton Dickinson FACSAria and FACSDiva software (Becton Dickinson, San Jose, Calif., USA). A total of 10,000 events were acquired.

4. Quantitative Real Time Polymerase Chain Reaction

The expressions of adipocyte-, osteocyte-, chondrocyte-, and tenocyte-specific genes were examined by quantitative real time polymerase chain reaction (qPCR). First, total RNA was extracted from cells by using a HiYield Total RNA Mini kit (Real Biotech Corporation, Taiwan). After the absorbances were measured at 260 nm and 280 nm using a spectrophotometer (NanoDrop, Wilmington, Delaware), the total RNA in explants was quantified. 1 µg of each total RNA was mixed with 50 µM oligo (dT) and 10 mM dNTP and distilled water was added to the mixture until a final volume of 10 The reaction was allowed to proceed at 65° C. for 5 min. Thereafter, the reaction solution was mixed with a mixed solution of 10×RT buffer, 25 mM MgCl$_2$, 0.1 M DTT, 40 U/ml RNaseOut, and 200 U/mL Superscript II Reverse Transcriptase (Superscript II Reverse Transcription kit (Invitrogen, Carlsbad, California)). The mixture was allowed to react at 50° C. for 50 min and at 85° C. for 5 min. The resulting solution was cooled to 4° C. and a 2 U/ml RNase H solution was added thereto. The reaction was allowed to proceed at 37° C. for 20 min to synthesize cDNA. Taq-Man Gene Expression Assays (Applied Biosystems, Foster City, California) were used in real time to quantify the expression of the following genes: aP2 (assay ID: Hs01086177_m1), OPN (assay ID: Hs00959010_m1), Aggrecan (assay ID: Hs00153936_m1), SCX A/B (assay ID: Hs03054634_g1), and GAPDH (assay ID: Hs99999905_m1). Polymerase chain reaction was performed on a LightCycler 480 (Roche Applied Science, Mannheim, Germany). The polymerase chain reaction consisted of 60 cycles of denaturation (95° C./10 min) and annealing (95° C., 10 sec, 60° C./1 min, 72° C./4 sec). The polymerization was performed at 72° C. for 7 min and the results were observed. Gene expression was quantified compared to the expression level of GAPDH as a control.

EXAMPLES

<Examples 1-5> Culture of Umbilical Cord-Derived Stem Cells

Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 μg/ml streptomycin sulfate, and 0.25 μg/ml amphotericin B (antibiotic-antimycotic solution; Welgene, Daegu, Korea)) to remove residual blood from the outer surface, and then its length and weight were measured. The massive umbilical cord was uniformly cut into pieces with scissors such that each piece had a width of ~5 cm, a length of ~5 cm, and a height of ~5 cm. The umbilical cord tissue was chopped into explants with different sizes: ≤1 mm (Example 1), 1-2 mm (Example 2), 2-4 mm (Example 3), >4 mm (Example 4), ≤10 mm (Example 5) in each of width, length, and height. The explants were aligned in and inoculated into a culture dish containing sterile DMEM medium. After the explants completely adhered to the culture dish, a culture medium was added to the culture dish.

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/$cm^2$.

<Example 6> Culture of Umbilical Cord-Derived Stem Cells with or without Culture Medium for Explantation Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 μg/ml streptomycin sulfate, and 0.25 μg/ml amphotericin B (antibiotic-antimycotic solution; Welgene, Daegu, Korea)) to remove residual blood from the outer surface, and then its length and weight were measured.

Since the collected umbilical cord was massive and viscous, much time is required to cut the umbilical cord with scissors. For isolating a large number of cells in a short time, 0-5 ml of a culture medium was added per gram of the collected umbilical cord tissue, and thereafter, the umbilical cord tissue was explanted to a width of 2-4 mm, a length of 2-4 mm, and a height of 2-4 mm. The explants were aligned in and inoculated into a culture dish. After the explants completely adhered to the culture dish, a culture medium was added to the culture dish.

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/$cm^2$.

<Example 7> Culture of Umbilical Cord Tissue-Derived Stem Cells after Inoculation with Different Initial Amounts of Umbilical Cord Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 μg/ml streptomycin sulfate, and 0.25 μg/ml amphotericin B (antibiotic-antimycotic solution; Welgene, Daegu, Korea)) to remove residual blood from the outer surface, and then its length and weight were measured.

The umbilical cord tissue was explanted to a width of 2-4 mm, a length of 2-4 mm, and a height of 2-4 mm. The explants were aligned in and inoculated into a culture dish. The explants were added in an amount of 0-13.5 mg per unit area ($cm^2$) of the culture dish. After the explants completely adhered to the culture dish, a culture medium was carefully added to the culture dish.

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/$cm^2$.

<Example 8> Culture of Umbilical Cord Tissue-Derived Stem Cells for Different Adherence Times Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 μg/ml streptomycin sulfate, and 0.25 μg/ml amphotericin B (antibiotic-antimycotic solution; Welgene, Daegu, Korea)) to remove residual blood from the outer surface, and then its length and weight were measured.

The umbilical cord tissue was explanted to a width of 2-4 mm, a length of 2-4 mm, and a height of 2-4 mm. The explants were allowed to adhere to a culture dish and left standing in a 5% $CO_2$ incubator at 37° C. for different times (10 min, 30 min, 60 min, 120 min, and 180 min).

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/$cm^2$.

<Example 9> Isolation of Cord-Derived Stem Cells when all Conditions were Met Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 μg/ml streptomycin sulfate, and 0.25 μg/ml amphotericin B (antibiotic-antimycotic solution; Welgene, Daegu, Korea)) to remove residual blood from the outer surface, and then its length and weight were measured. 0-2 ml of a culture medium was added per gram of the collected umbilical cord tissue. Thereafter, the umbilical cord tissue was explanted to a width of 2-4 mm, a length of 2-4 mm, and a height of 2-4 mm. The explants were aligned in and inoculated into a culture dish. The explants were added in an amount of 0.7-6.8 mg per unit area (cm$^2$) of the culture dish. The explants were allowed to stand in a 5% $CO_2$ incubator at 37° C. for 60 min.

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/cm$^2$.

<Comparative Example 1> Culture of Umbilical Cord Tissue-Derived Stem Cells

Umbilical cord was collected from a normal heavily pregnant woman with her consent after cesarean section or vaginal delivery. The umbilical cord was washed 2-3 times with $Ca^{2+}$, $Mg^{2+}$-free Dulbecco's phosphate-buffered saline (DPBS, Gibco) supplemented with antibiotics (100 U/ml penicillin, 100 µg/ml streptomycin sulfate, and 0.25 µg/ml amphotericin B (antibiotic-antimycotic solution; Welgene, Daegu, Korea)) to remove residual blood from the outer surface, and then its length and weight were measured. The massive umbilical cord was cut into ~5 cm pieces for uniform cutting with scissors.

The umbilical cord was chopped into explants having a width of 1-2 mm, a length of 1-2 mm and a height of 1-2 mm with scissors and a knife. Thereafter, the explants were treated with gentle stirring in low-glucose Dulbecco's modified Eagle medium (LG DMEM; Welgene, Daegu, Korea) supplemented with 0.1% type 1 collagenase (Sigma-Aldrich, St. Louis, MO, USA) and antibiotic at 37° C. for 2 h. After addition of the same amount of a culture medium (LG DMEM, 10% fetal bovine serum (FBS; Welgene, Daegu, Korea), and antibiotic-antimycotic solution), undigested tissues were removed using a 100-µm cell strainer. Cells were collected by centrifugation at 500 g and at 20° C. for 15 min and washed twice with the culture medium. The isolated cells were counted by trypan blue exclusion, placed at a density of 1×10$^4$ cells/cm$^2$ in a 150 mm culture dish, and cultured in a 5% $CO_2$ incubator at 37° C. 3 days after culture, the medium was replaced with a new one to remove cells remaining non-adherent to the bottom of the culture dish and the culture solution was replaced with new ones 2-3 times a week.

When cells have grown to a confluency of ~60-80% in the culture dish, the adherent cells were detached by washing twice with DPBS and treatment with a trypsin-EDTA solution (0.05% trypsin and 0.53 mM ethylenediamine tetraacetic acid (trypsin-EDTA; Welgene, Daegu, Korea) for 3 min. Thereafter, the cells were stained by trypan blue exclusion, counted, and continuously cultured at a density of 3,333 cells/cm$^2$.

Experimental Example 1. Measurement of Numbers of the Umbilical Cord-Derived Stem Cells Isolated in Examples 1-5 and Comparative Example 1

The cells collected in Examples 1-4 and Comparative Example 1 were counted. The results are shown in FIGS. 1A to 1C and Table 2.

Figure 1B:
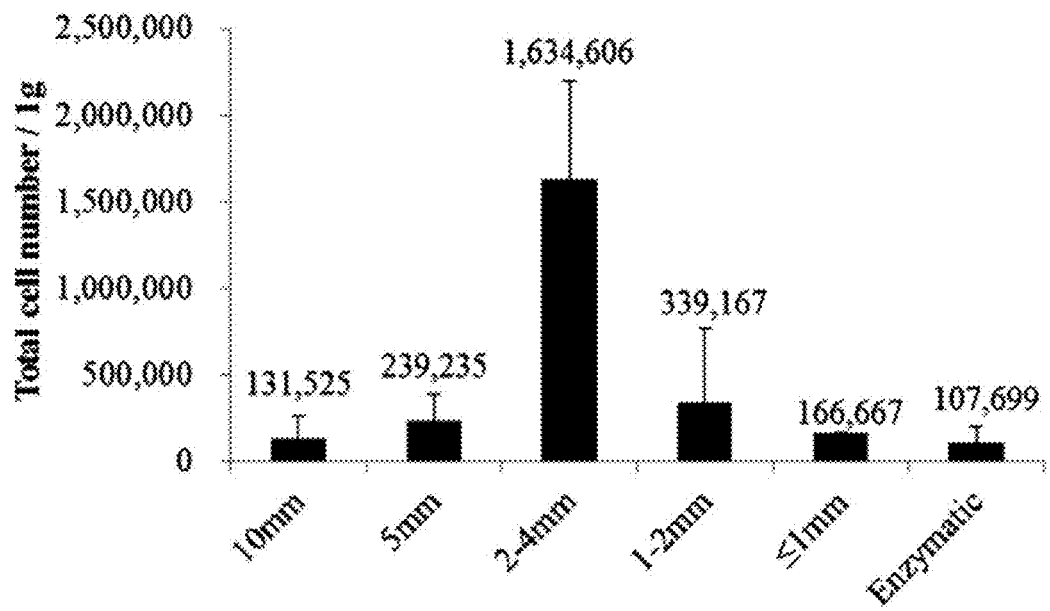
FIG. 1B shows the numbers of cells isolated from explants with different sizes prepared in Examples 1-5.
Figure 1C:
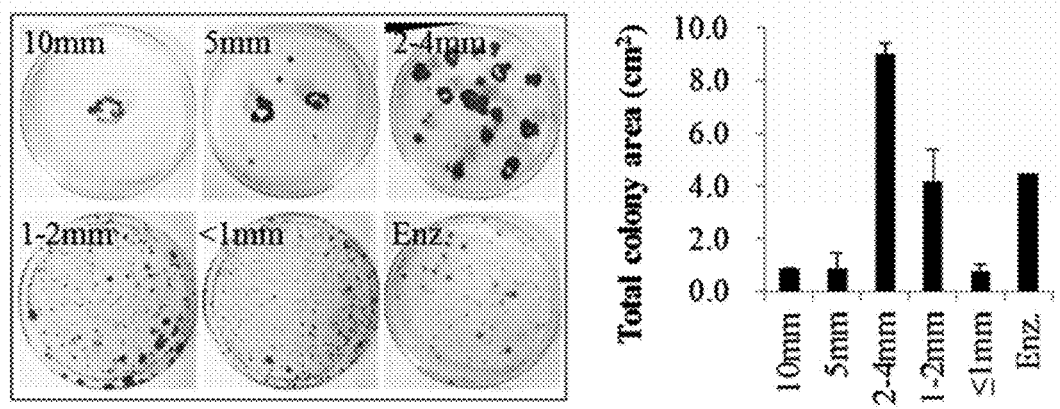
FIG. 1C shows the sizes of colonies formed after culture of explants with different sizes prepared in Examples 1-5.

In FIG. 1A shows changes in the numbers of the umbilical cord-derived stem cells as a function of chopping time by scissor in Examples 1-5, FIG. 1B shows the numbers of the umbilical cord-derived stem cells isolated from the explants with different sizes prepared in Examples 1-5, and FIG. 1C shows the sizes of colonies formed from the umbilical cord-derived stem cells after culture of the explants with different sizes prepared in Examples 1-5.

As shown in FIGS. 1A to 1C, the number of the cord-derived stem cells isolated in Example 3 was measured to be 1.86±0.49×10$^6$/g. The same result was also obtained from the result of CFU-F staining. That is, the number of the cells isolated in Example 3 was larger than those in Comparative Example 1 and Examples 1, 2, 4, and 5. It was also confirmed that 1 min-scissoring was most suitable to prepare the explants of Example 3, whose size is ideal for efficient cell isolation.

As a result of the 1 min-scissoring, the explants having a width of 2-4 mm, a length of 2-4 mm, and a height of 2-4 mm accounted for >50% of all explants. The umbilical cord-derived stem cells isolated from the explants of Example 3 proliferated very easily, which were demonstrated through the following experimental examples.

TABLE 2

| Size of explants | Number of isolated cells per gram of explants | Area of CFU-Fs per gram of explants (cm$^2$) |
|---|---|---|
| 10 mm (Example 5) | 148,720 ± 122,661 | 1.0 ± 0.2 |
| 5 mm (Example 4) | 264,138 ± 144,990 | 1.2 ± 0.5 |
| 2-4 mm (Example 3) | 1,855,818 ± 490,340 | 9.0 ± 0.4 |
| 1-2 mm (Example 2) | 320,000 ± 208,046 | 4.2 ± 1.2 |
| <1 mm (Example 1) | 123,333 ± 61,283 | 0.8 ± 0.3 |
| Comparative Example 1 | 432,830 ± 258,225 | 4.5 ± 0.0 |

Experimental Example 2: Measurement of Numbers of the Cells Isolated in Example 6

Figure 2A:
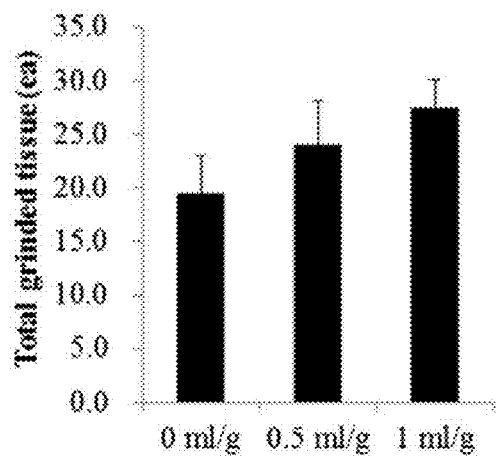
FIG. 2A shows the total ground tissues obtained by explantation of an umbilical cord tissue in culture dishes containing different amounts of a medium (0 ml/g, 0.5 ml/g, and 1 ml/g)
Figure 2B:
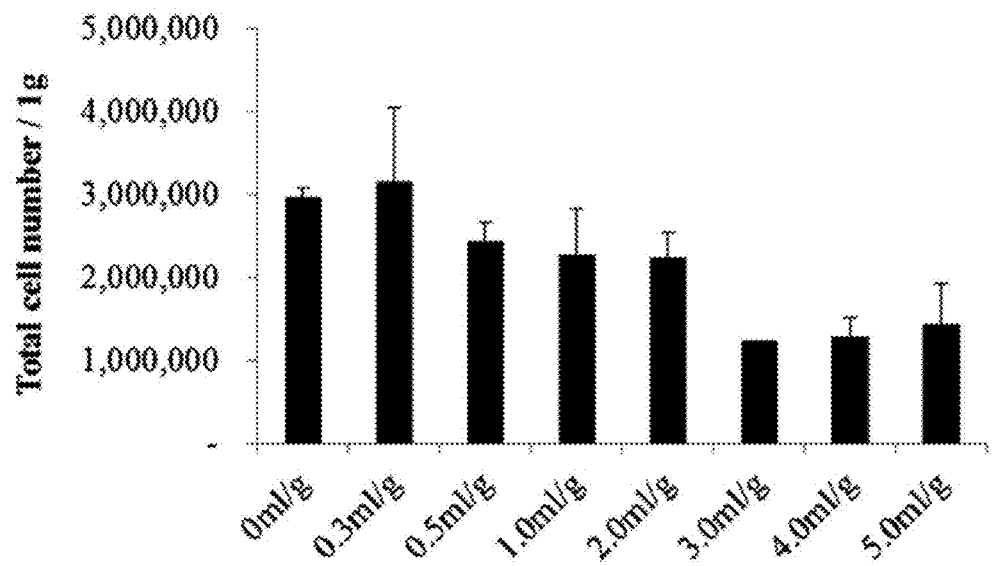
FIG. 2B shows the total numbers of cells isolated by explantation of an umbilical cord tissue in culture dishes containing different amounts of a medium (0 ml/g, 0.3 ml/g, 0.5 ml/g, 1 ml/g, 2 ml/g, 3 ml/g, 4 ml/g, and 5 ml/g).

In FIG. 2A shows the total ground tissues obtained by explantation of the umbilical cord tissue in culture dishes containing different amounts of the medium (0 ml/g, 0.5 ml/g, and 1 ml/g) and FIG. 2B shows the total numbers of the cells isolated by explantation of the umbilical cord tissue in culture dishes containing different amounts of the medium (0 ml/g, 0.3 ml/g, 0.5 ml/g, 1 ml/g, 2 ml/g, 3 ml/g, 4 ml/g, and 5 ml/g).

TABLE 3

| Amount of culture medium | Number of explants |
|---|---|
| 0 ml/g | 19.5 ± 3.5 |
| 0.5 ml/g | 24.0 ± 4.1 |
| 1.0 ml/g | 27.5 ± 2.6 |

TABLE 4

| Amount of medium | Number of isolated cells per gram of explants |
|---|---|
| 0.5 ml/g | 2,190,000 ± 189,934 |
| 1.0 ml/g | 1,990,000 ± 328,976 |
| 2.0 ml/g | 2,233,333 ± 267,815 |
| 3.0 ml/g | 1,510,000 ± 442,691 |
| 4.0 ml/g | 1,446,667 ± 285,832 |
| 5.0 ml/g | 1,503,333 ± 311,328 |

As can be seen from the results in FIGS. 2A to 2B and Tables 3 and 4, the umbilical cord tissue was chopped into larger numbers of smaller pieces in the medium. Different amounts (0, 0.3, 0.5, 1.0, 2.0, 3.0, 4.0, and 5.0 ml) of the culture medium were added to 1 gram of the umbilical cord tissue, the umbilical cord was cut, and the cells were counted when 80% confluence was reached. The umbilical cord tissue was cut into small explants and the number of isolated cells decreased with increasing amount of the medium.

The amount of the culture medium per gram of the umbilical tissue was found to be 0-5.0 ml, preferably 0.5-3 ml. Specifically, the number of the explants increased by 1.4 times when the umbilical tissue was cut in the presence of the medium than in the absence of the medium.

Significantly larger areas of CFU-Fs were obtained when the umbilical cord-derived stem cells of Example 3 were used than when the other sized explants were used. In particular, the total area of CFU-Fs was $9.0\pm0.4$ cm$^2$ for the explants of Example 3, where the 2-4 mm-sized explants per gram of the explants accounted for ≥50% of all explants, $4.2\pm1.2$ cm$^2$ for the explants of Example 2, and $4.5\pm0.0$ cm$^2$ for the explants of Comparative Example 1.

Experimental Example 3: Measurement of Numbers of the Cells Isolated from Different Amounts of the Explants The explants were transferred to a 150 mm culture dish and a change in the number of the cells isolated from different weights (g) of the explants was investigated. 0.1, 0.5, 1.0, and 2.0 g of the 2-4 mm explants were aligned in the 150 mm culture dish, followed by culture for 2 weeks. When 80% confluence was reached, the number of isolated cells was measured and the number of CFU-Fs was measured.

Figure 3A:
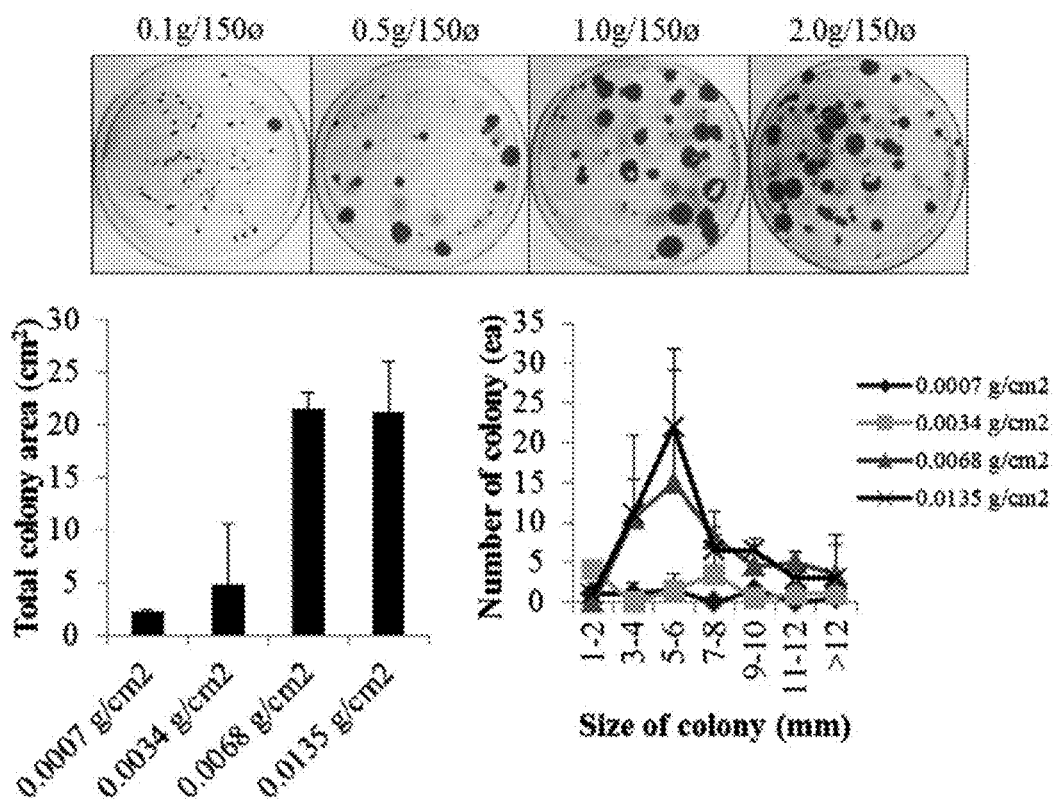
FIG. 3A shows the numbers of CFU-Fs from umbilical cord-derived stem cells isolated from different weights of explants, where the CFU-F numbers were determined by crystal violet staining and the bottom graphs show the numbers and sizes of CFU-Fs.
Figure 3B:
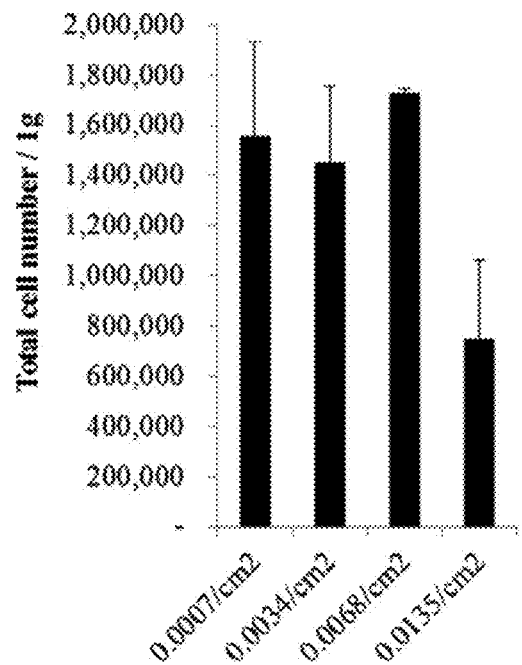
FIG. 3B shows the numbers of umbilical cord-derived stem cells isolated from different weights of explants.

In FIG. 3A shows the numbers of CFU-Fs from the umbilical cord-derived stem cells isolated from different weights of the explants, where the CFU-F numbers were determined by crystal violet staining and the bottom graphs show the numbers and sizes of CFU-Fs and FIG. 3B shows the numbers of the umbilical cord-derived stem cells isolated from different weights of the explants.

TABLE 5

| Amount of umbilical cord inoculated | Area of CFU-Fs per gram of explants (cm$^2$) |
|---|---|
| 0.1 g | $2.2 \pm 0.2$ |
| 0.5 g | $4.8 \pm 5.7$ |
| 1.0 g | $21.5 \pm 1.6$ |
| 2.0 g | $21.2 \pm 4.9$ |

As shown in FIGS. 3A to 3B and Table 5, there were no significant differences in the number of cells isolated from different weights of the explants but the number of colonies increased with increasing weight of the explants. Particularly, there were significant differences in the number of colonies from the cord-derived stem cells isolated from 0.1 g, 0.5 g, and 1.0 g or 2.0 g, but no difference was observed in the number of colonies from the cord-derived stem cells isolated from 1.0 g and 2.0 g of the explants.

Moreover, when considering the weight of the explants per unit area of the culture dish (0.0007-0.0135 g/cm$^2$), the number of the isolated cord-derived stem cells from 2.0 g of the explants in the culture dish was reduced. That is, the excessively large weight of the umbilical cord tissue (Example 5) led to a reduction in the number of the umbilical cord-derived adult stem cells isolated from different weights of the explants. These results revealed that when the explants were cultured to reach 0.0007-0.0068 g/cm$^2$, the largest number of umbilical cord-derived stem cells could be obtained.

Experimental Example 4: Analysis of Numbers of Isolated Umbilical Cord-Derived Stem Cells after Culture for Different Adherence Times The umbilical cord-derived stem cells produced in Example 8 were allowed to adhere to a $CO_2$ incubator, followed by culture for 10, 30, 60, 120, and 180 min. The numbers of cells adherent to the incubator were measured and the numbers of CFU-Fs were measured to evaluate the effect of the adherence time.

Figure 4A:
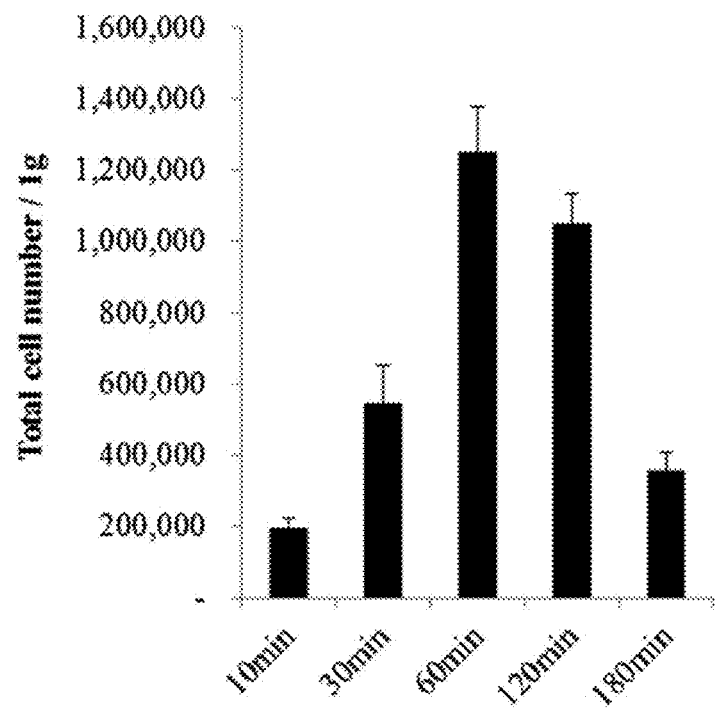
FIG. 4A shows the numbers of umbilical cord-derived stem cells isolated in Example 8 and FIG. 4B shows the numbers of CFU-Fs from umbilical cord-derived stem cells produced in Example 8, where the CFU-F numbers were determined by crystal violet staining and the bottom graphs show the numbers and sizes of CFU-Fs.
Figure 4B:
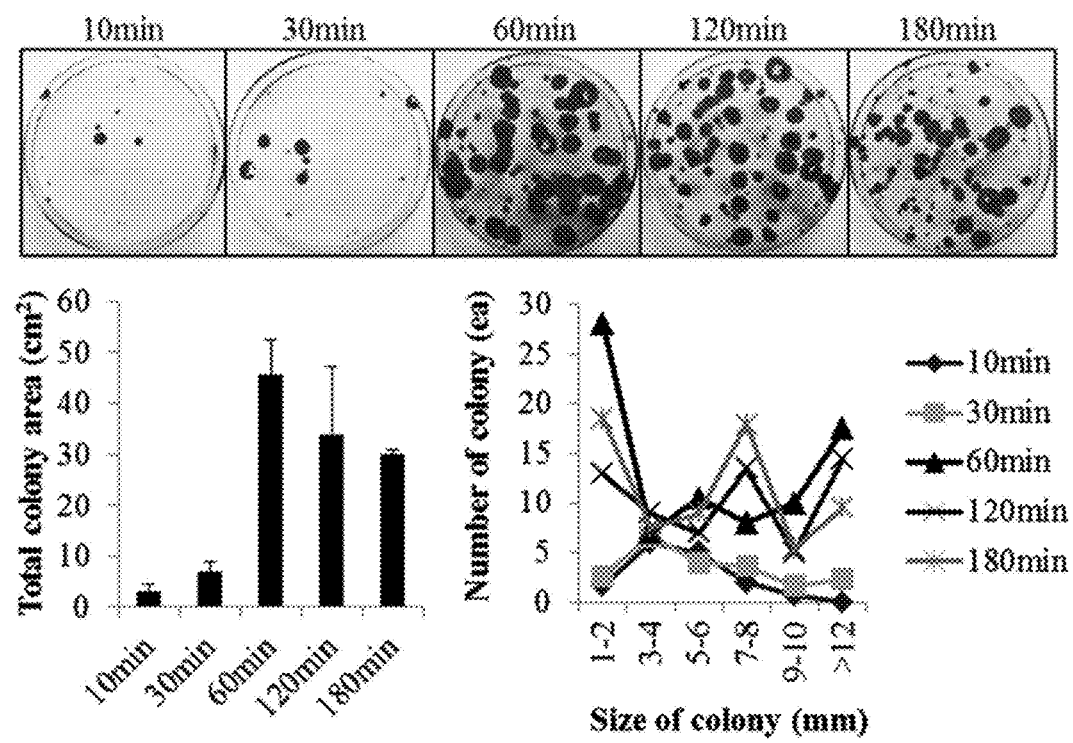

In FIG. 4A shows the numbers of umbilical cord-derived stem cells isolated in Example 8 and FIG. 4B shows the numbers of CFU-Fs from the umbilical cord-derived stem cells produced in Example 8, where the CFU-F numbers were determined by crystal violet staining and the bottom graphs show the numbers and sizes of CFU-Fs.

TABLE 6

| Adherence time | Number of isolated cells per gram of explants | Area of CFU-Fs per gram of explants (cm$^2$) |
|---|---|---|
| 10 min | $195{,}000 \pm 28{,}284$ | $3.1 \pm 1.2$ |
| 30 min | $552{,}500 \pm 109{,}602$ | $6.9 \pm 2.0$ |
| 60 min | $1{,}250{,}000 \pm 127{,}279$ | $45.7 \pm 6.9$ |
| 120 min | $980{,}000 \pm 77{,}782$ | $33.9 \pm 13.5$ |
| 180 min | $360{,}000 \pm 49{,}497$ | $29.9 \pm 1.0$ |

As shown in FIGS. 4A to 4B and Table 6, as the adherence time of the explants increased, the number of isolated cells increased gradually. The maximum number of isolated cells was observed when the explants adhered for 60 min.

However, the number of isolated cells began to decrease gradually when the adherence time exceeded 120 min. The same tendency was also observed when the number of CFU-Fs was measured. Specifically, the maximum area ($45.7\pm6.9$ cm$^2$) of CFU-Fs was achieved when the adherence time was 60 min and the areas of CFU-Fs when the adherence times were 120 and 180 min were not significantly different from that when the adherence time was 60 min.

Taken together, it is most preferable that the explants of the umbilical cord tissue are 2-4 mm in each of width, length and height and are aligned and cultured in an incubator for 60 min.

Experimental Example 5: Growth Characteristics

In this example, the population doubling time (PDT) of umbilical cord-derived stem cells collected from a culture medium was measured. To this end, the cells produced in Example 9 were seeded and cultured in a 48-multiwell culture dish. The PDT was calculated by PDT=[(days in exponential phase)/((log N2−log N1)/log 2)], where N1 is the number of cells at the initial stage of the exponential growth phase and N2 is the number of cells at the end of the exponential growth phase.

Figure 5A:
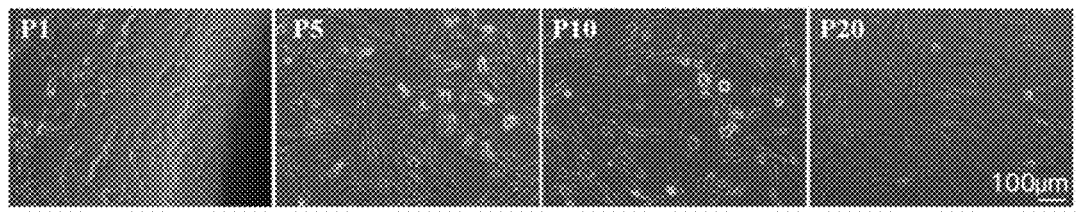
FIG. 5A shows optical microscopy images showing the morphologies of umbilical cord-derived stem cells produced in Example 9.
Figure 5B:
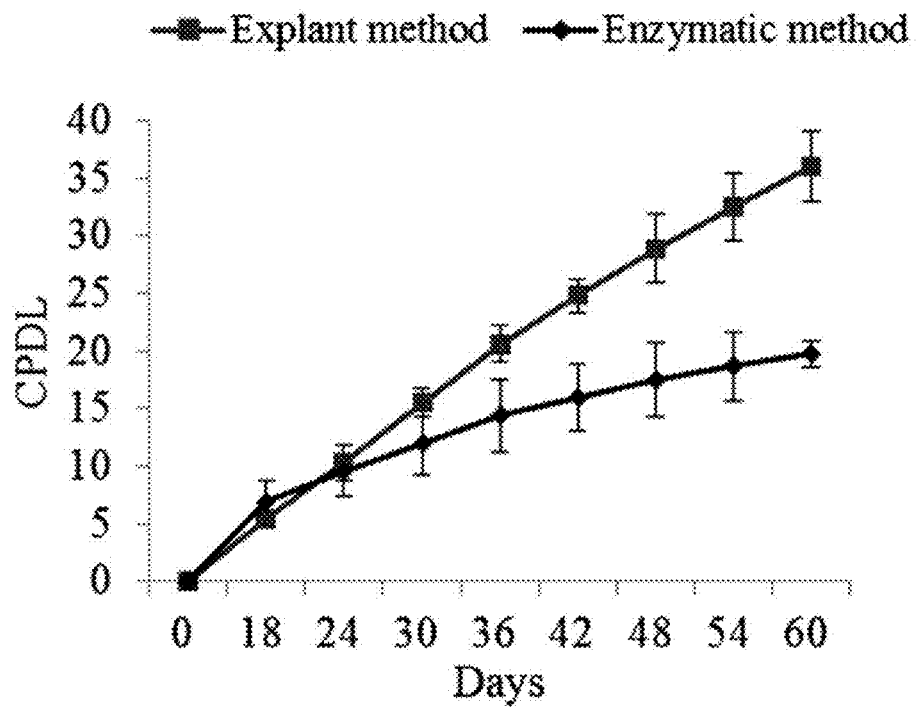
FIG. 5B shows culture time-dependent changes in the CPDL of umbilical cord-derived stem cells produced by an enzymatic method in Comparative Example 1 and umbilical cord-derived stem cells produced in Example 9.
Figure 5C:
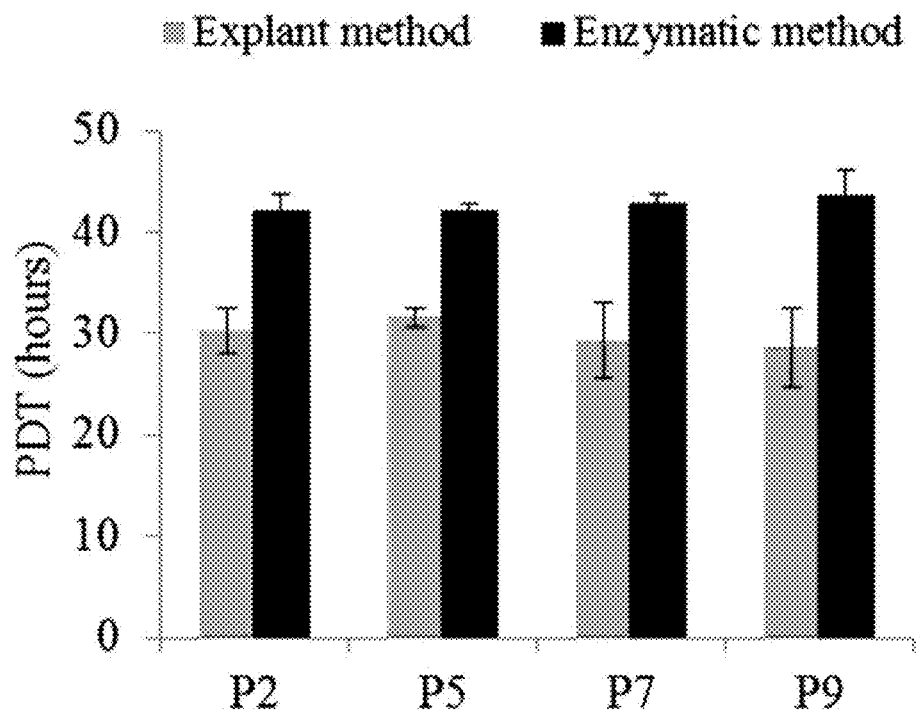
FIG. 5C shows population doubling time (PDT) values of umbilical cord-derived stem cells produced by an enzymatic method in Comparative Example 1 and umbilical cord-derived stem cells produced in Example 9.

In FIG. 5A shows optical microscopy images showing the morphologies of the umbilical cord-derived stem cells produced in Example 9, FIG. 5B shows culture time-dependent changes in the CPDL of the umbilical cord-derived stem cells produced by an enzymatic method in Comparative Example 1 and the umbilical cord-derived stem cells produced in Example 9, and FIG. 5C shows population doubling time (PDT) values of the umbilical cord-derived stem cells produced by an enzymatic method in Comparative Example 1 and the umbilical cord-derived stem cells produced in Example 9.

TABLE 7

| Number of subcultures | Population Doubling Time (hr) | |
|---|---|---|
| | Umbilical cord-derived stem cells produced by enzymatic method in Comparative Example 1 | Umbilical cord-derived stem cells produced in Example 9 |
| P2 | 42.1 ± 1.7 | 30.3 ± 2.0 |
| P5 | 42.1 ± 0.7 | 31.6 ± 0.7 |
| P7 | 42.8 ± 1.0 | 28.6 ± 3.7 |
| P9 | 43.5 ± 2.7 | 27.6 ± 3.2 |

As shown in FIG. 5A, the umbilical cord-derived stem cells obtained by the inventive method had a spindle shape and maintained their characteristic fibroblast-like shape even after subcultures.

As shown in FIGS. 5B and 5C, the CPDL values of the umbilical cord-derived stem cells produced in Example 9 were 35.5±2.36 and 55.8±1.96 after culture for 60 and 88 days, respectively, which are significantly higher than those of the umbilical cord-derived stem cells produced in Comparative Example 1 and those previously reported.

As shown in FIGS. 5A to 5C and Table 7, the umbilical cord-derived stem cells produced in Example 9 showed significantly lower PDT values at stages P2, P5, P7, and P9 than the umbilical cord-derived stem cells isolated in Comparative Example 1. No change was observed in the PDT of the umbilical cord-derived stem cells produced in Example 9 Even when the Number of Subcultures Increased.

Experimental Example 6: Immunophenotyping

Immunophenotyping was performed as described above. Mesenchymal stem cells are generally known to be positive for CD73, CD90, and CD105 while negative for CD11b (or CD14), CD19 (or CD79 alpha), CD34, CD45, and HLA-DR. Under the assumption that the umbilical cord-derived stem cells isolated by the inventive method show this propensity, the analysis was conducted.

Figure 6:
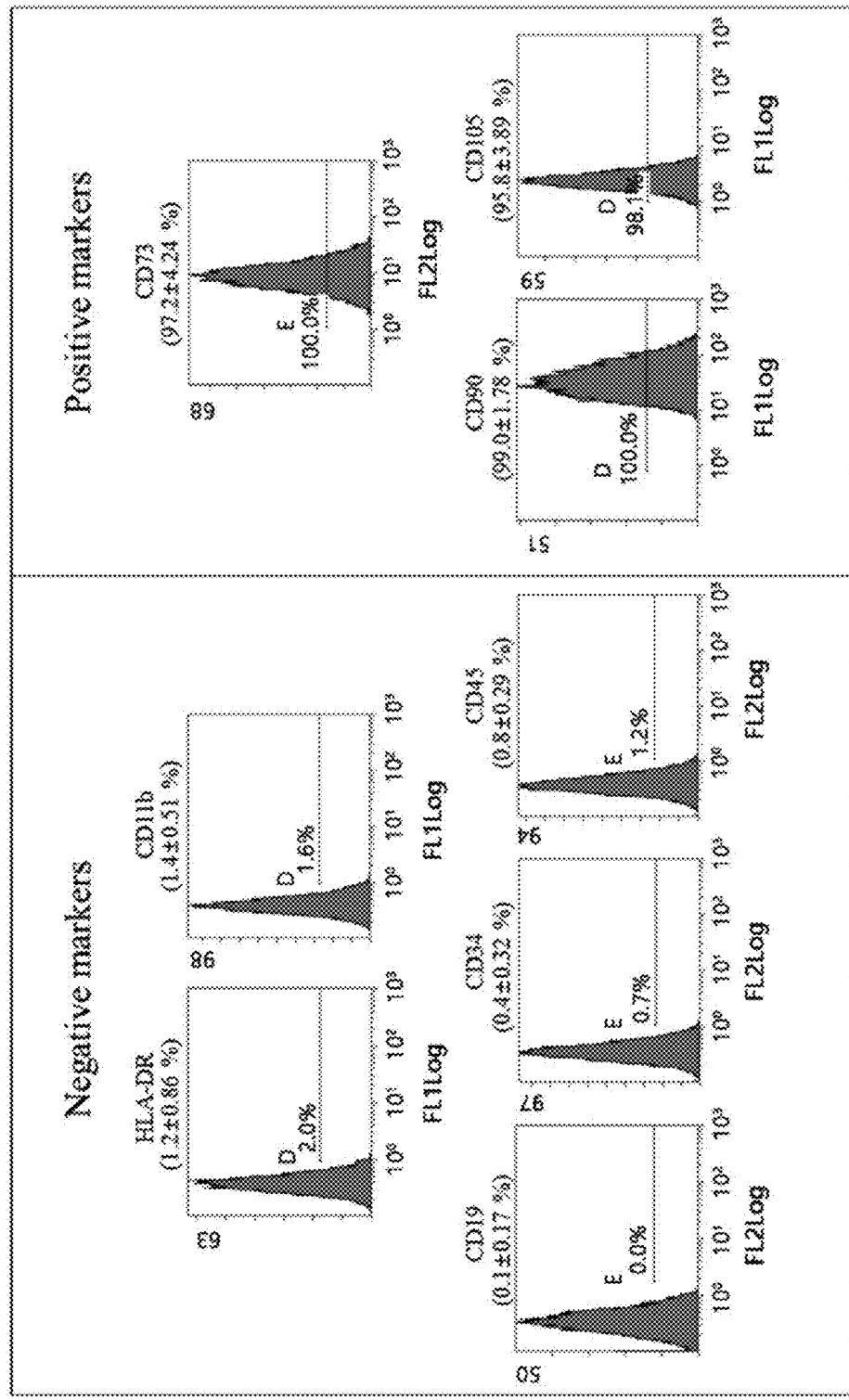
FIG. 6 shows the immunophenotypic characteristics of umbilical cord-derived stem cells isolated in Example 9, which were analyzed using a flow cytometer.

FIG. 6 shows the immunophenotypic characteristics of the umbilical cord-derived stem cells isolated in Example 9, which were analyzed using a flow cytometer. The results are summarized in Table 8. The umbilical cord-derived stem cells isolated in Example 9 were strongly positive for CD73, CD90, and CD105 (>95%) but negative for HLA-DR, CD11b, CD19, CD34, and CD45 (<1.5%).

TABLE 8

| Marker | Positive rate |
|---|---|
| CD73 | 97.2 ± 4.2 |
| CD90 | 99.0 ± 1.8 |
| CD105 | 95.8 ± 3.9 |
| CD11b | 1.4 ± 0.5 |
| CD19 | 0.1 ± 0.2 |
| CD34 | 0.4 ± 0.3 |
| CD45 | 0.8 ± 0.3 |
| HLA-DR | 1.2 ± 0.9 |

Experimental Example 7: Multipotency of Umbilical Cord-Derived Stem Cells

1) Ability to Differentiate into Adipocytes

The ability of the umbilical cord-derived stem cells produced in Example 9 to differentiate into adipocytes was evaluated. To this end, first, the cells were put at a density of 8,000 cells/cm$^2$ in a culture dish. After ~60-80% confluency was reached, the cells were cultured in an adipocyte differentiation culture medium (LG-DMEM) supplemented with 10% fetal bovine serum, 1% antibiotic solution, 0.5 mM 3-isobutyl-1-methylxantine (Sigma), 1 μM dexamethasone, 5 μg/ml insulin (Gibco), and 60 μM indomethacin (Sigma) for 21 days. The degree of differentiation of the cells was measured by Oil Red O staining and gene expression of adipocyte markers. For Oil Red O staining, the cultured cells were washed once with distilled water, fixed in 4% paraformaldehyde at room temperature for 1 h, washed 3 times, reacted with a 0.18% Oil Red O solution (Sigma) at room temperature for 10 min, washed with distilled water, and observed for differentiation into adipocytes.

Figure 7A:
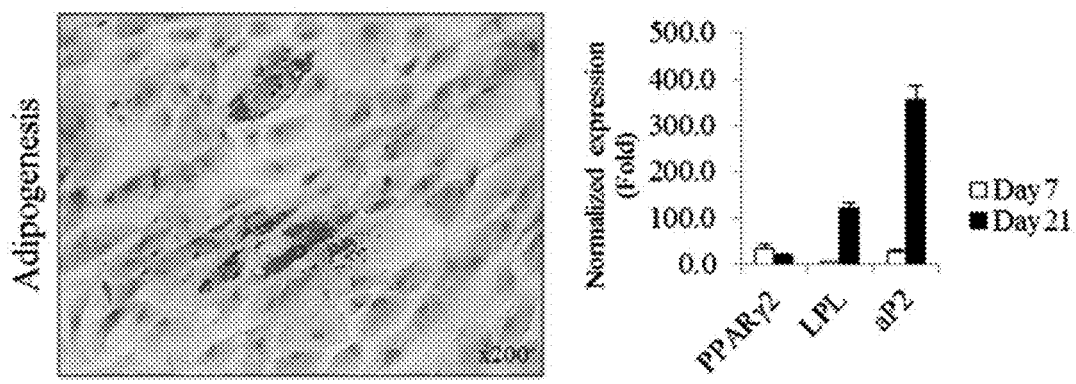
FIGS. 7A to 7D show the differentiation potentials of umbilical cord-derived stem cells isolated in Example 9 for adipogenesis (FIG. 7A), osteogenesis (FIG. 7B), chondrogenesis (FIG. 7C), and tenogenesis (FIG. 7D).
Figure 7B:
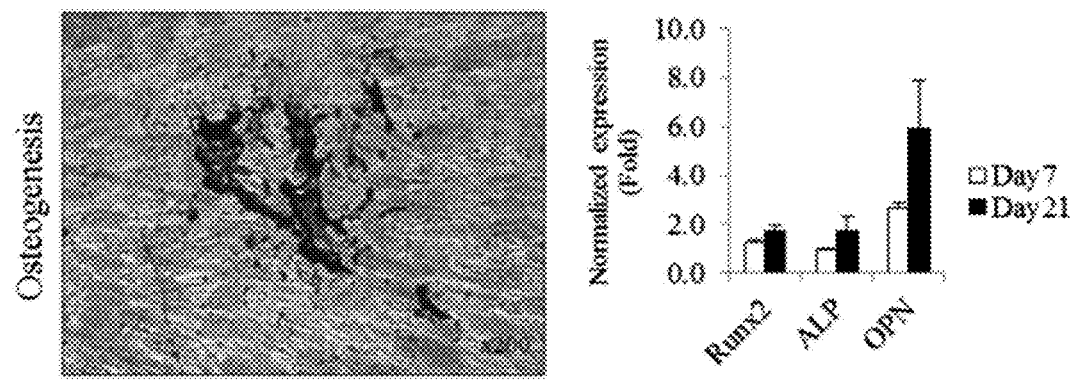
Figure 7C:
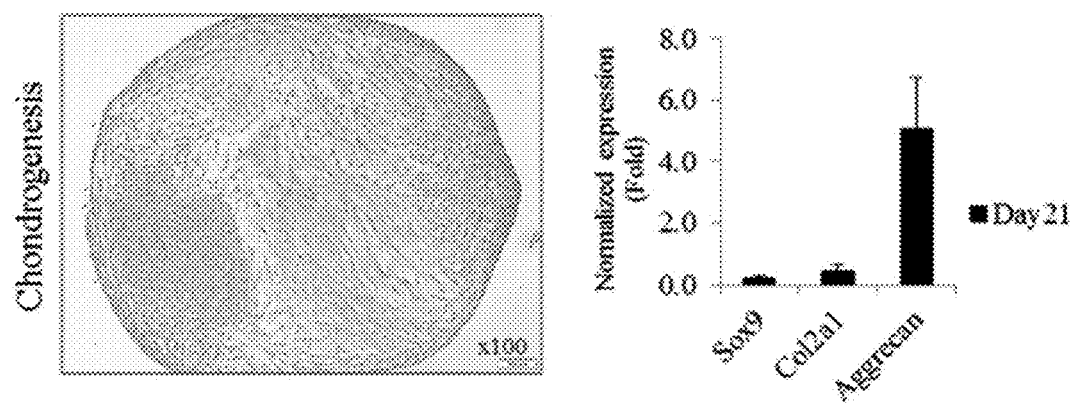
Figure 7D:
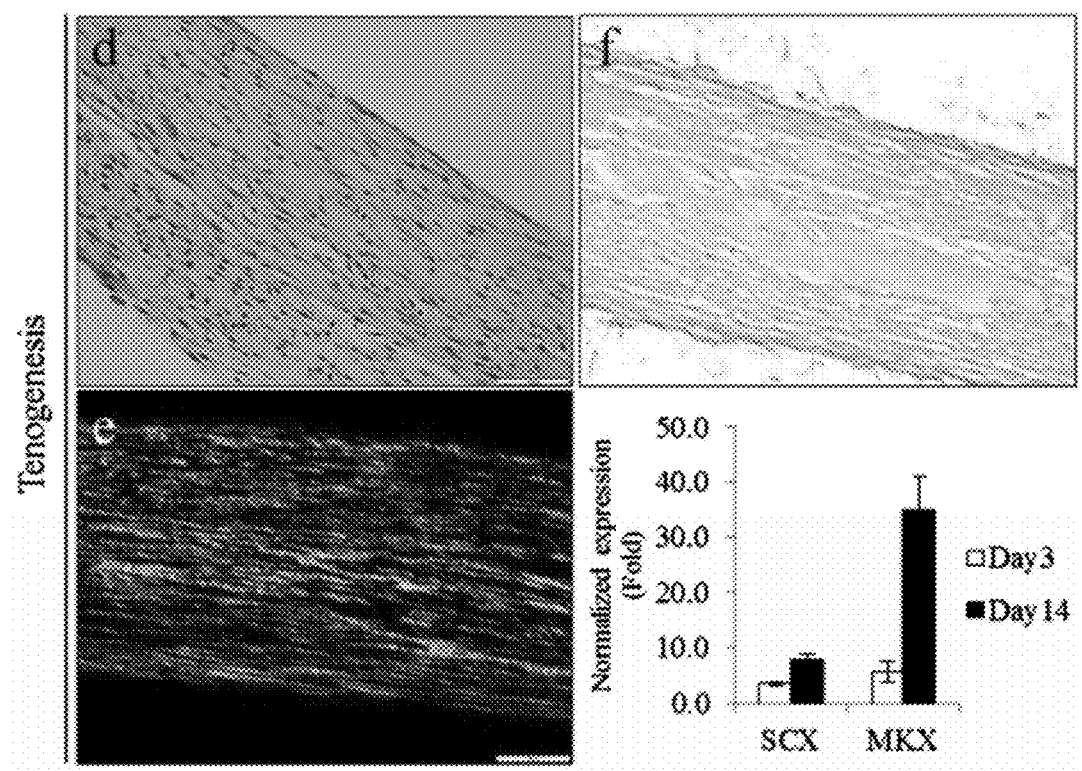

FIGS. 7A to 7D show the differentiation potentials of the umbilical cord-derived stem cells isolated in Example 9 for adipogenesis (FIG. 7A), osteogenesis (FIG. 7B), chondrogenesis (FIG. 7C), and tenogenesis (FIG. 7D).

As shown in FIG. 7A, the differentiation of the umbilical cord-derived stem cells into adipocytes was induced and then neutral lipid accumulation was observed (PPARγ2). The neutral lipids were represented in red. Significantly increased expressions of lipoprotein lipase (LPL) and adipocyte protein 2 (aP2) were observed. Specifically, the expression of the adipocyte differentiation marker, aP2, in the differentiated cells was found to be 355±31.94-fold higher than that in the undifferentiated cells.

2) Ability to Differentiate into Osteocytes

The ability of the umbilical cord-derived stem cells isolated in Example 9 to differentiate into osteocytes was evaluated. To this end, first, the cells were put at a density of 8,000 cells/cm$^2$ in a culture dish. After ~60-80% confluency was reached, the cells were cultured in an osteocyte differentiation culture medium (LG-DMEM) supplemented with 10% fetal bovine serum, 1% antibiotic solution, 100 nM dexamethasone (Sigma, St. Louis, MO, USA), 10 mM β-glycerophosphate (Sigma), and 0.2 mM ascorbic acid 2-phosphate (Sigma) for 21 days. The degree of differentiation of the cells was measured by Von Kossa staining and gene expression of osteocyte markers. For Von Kossa staining, the cultured cells were washed once with distilled water, fixed in 4% paraformaldehyde at room temperature for 1 h, washed 3 times, reacted with a 5% silver nitrate solution (Sigma) under a 60 W lamp for 1 h, washed three times with distilled water, treated with 5% sodium thiosulfate for 5 min, reacted with 0.1% nuclear fast red solution for 5 min, and observed for differentiation into osteocytes.

As shown in FIG. 7B, the presence of extracellular calcium was confirmed and the expression levels of Runt-related transcription factor 2 (Runx2), alkaline phosphatase (ALP), and osteopontin (OPN) in the differentiated cells were significantly higher than those in the undifferentiated cells. The expression levels were measured by real-time PCR. Specifically, the expression of the osteocyte differentiation marker, OPN, in the differentiated cells was found to be 5.9±1.94-fold higher than that in the undifferentiated cells. These results lead to the conclusion that the inventive umbilical cord-derived stem cells can differentiate into osteoblasts.

3) Ability to Differentiate into Chondrocytes

The ability of the umbilical cord-derived stem cells produced in Example 9 to differentiate into chondrocytes was evaluated. To this end, 2×10$^5$ umbilical cord-derived stem cells were suspended in HG-DMEM medium free of fetal bovine serum, placed in a 15 ml polypropylene tube, and centrifuged to obtain pellets for three-dimensional culture. The pellets were cultured in a differentiation medium (DMEM-HG) supplemented with 50 µg/ml ascorbic acid 2-phosphate, 100 nM dexamethasone, 100 µg/ml sodium pyruvate, 40 µg/ml proline, 10 ng/ml transforming growth factor-01, and 1× Insulin-Transferrin-Serenite (ITS; Gibco) for 21 days. The degree of differentiation of the cells into chondrocytes was measured by Safranin O staining and gene expression of chondrocyte markers. For Safranin O staining, the pellets were fixed in 4% paraformaldehyde solution at 4° C. for 24 h and 5 µm samples were then prepared. The samples were stained with a 0.2% safranin O solution for 10 min, washed with distilled water, reacted with a 0.04% fast green solution for 15 sec, and observed for differentiation into chondrocytes.

As shown in FIG. 7C, Safranin 0-stained aggrecan was found in the differentiated umbilical cord-derived stem cells, indicating that the differentiated cells efficiently differentiated into chondrocytes compared to the undifferentiated cells. The expression of the chondrocyte differentiation marker, Aggreca, in the differentiated cells was found to be 5.1±1.65-fold higher than that in the undifferentiated cells. These results lead to the conclusion that the inventive umbilical cord-derived stem cells can differentiate into chondrocytes.

4) Ability to Differentiate into Tenocytes

The ability of the umbilical cord-derived stem cells produced in Example 9 to differentiate into tenocytes was evaluated. To this end, first, SYLGARD (Dow Corning, Midland, MI, USA) was poured into a 35 mm culture dish and coated on the culture dish over 1-2 weeks. Then, 5 mm silk sutures were embedded in the SYLGARD. The culture dish and the sutures were sterilized with 100% ethanol and UV in a clean bench and dried for 2 h. Then, DMEM was pre-soaked in a $CO_2$ incubator at 37° C. for 1 h. 2×10$^5$ cells were mixed with a thrombin mixture (DMEM supplemented with 10% fetal bovine serum, 1% antibiotic solution, 1 U/ml thrombin (Merck Chemicals, UK), 200 µM aminohexanoic acid (Sigma-Aldrich), and 10 mg/ml aprotinin (Roche, UK)), and a 10 mg/ml fibrinogen solution (Sigma-Aldrich) was added thereto. The mixed solution was quickly spread on the surface of the SYLGARD-coated culture dish and allowed to stand at 37° C. for 1 h. Then, the cells were cultured in a tenocyte differentiation culture solution containing 250 µM ascorbic acid and 50 µM L-proline in DMEM-HG for 14 days. The degree of differentiation of the cells was measured by hematoxylin and eosin (H&E) staining, picrosirius red staining, and immunohistochemical staining. The degree of differentiation of the cells was also measured by gene expression of tenocyte markers. The cells were fixed in 4% paraformaldehyde solution for 24 h, embedded in paraffin to prepare 10 µm sectioned samples, followed by H&E staining and picrosirius red staining. For immunohistochemical staining, the cells were reacted with anti-Col I (Abcam), which had been previously diluted 1:200, at room temperature for 2 h, reacted with a HRP-conjugated secondary antibody at room temperature for 30 min, and observed for differentiation into tenocytes.

FIG. 7D confirmed the existence of fibrin structures aligned along the long axis. Specifically, H&E staining revealed the presence of a light-red stained matrix similar to a healthy tendon matrix and spindle-like cells. The tendon matrix was collagen type 1, which was colored yellow by picrosirius red staining. Immunohistochemical staining with a collagen type 1 antibody reconfirmed that the matrix was collagen type 1.

The expression levels of Scleraxis (SCX) and Mohawk (MKX) in the cells differentiated from the umbilical cord-derived stem cells produced in Example 9 were significantly higher than those in the undifferentiated cells. The expression levels were determined by real-time PCR. Specifically, the expression level of SCX was 57.4±1.97 times higher in the differentiated cells than that in the undifferentiated cells, demonstrating the ability of the inventive umbilical cord-derived stem cells to differentiate into tenocytes.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

The invention claimed is:

1. A method for isolating stem cells from umbilical cord tissue comprising:
   (a) grinding the umbilical cord tissue into hexahedral explants having a width of 2 to 4 mm, a length of 2 to 4 mm, and a height of 2 to 4 mm;
   (b) seeding the explants to a culture dish and culturing the explants in a first culture medium to reach 0.0007 to 0.0068 g per unit area of the culture dish as measured in cm$^2$ without enzymatic treatment; and
   (c) collecting the stem cells after culture;
   wherein step (a) further comprises introducing the umbilical cord tissue into a second culture medium before grinding the isolated umbilical cord tissue and the second culture medium is added in an amount of 0.5 to 3.0 ml per gram of the umbilical cord tissue;
   wherein adherence time of the explants to the culture dish in step (b) is carried out for 60 to 120 minutes.

2. The method according to claim 1, wherein step (c) is carried out when the stem cells are cultured to cover 60 to 90% of the surface area of the culture dish.

3. The method according to claim 1, wherein step (c) is carried out by treatment with trypsin-EDTA.

4. The method according to claim 1, wherein the first culture medium is selected from the group consisting of Dulbecco's minimum essential medium (DMEM), RPMI, Ham's F-10, Ham's F-12, α-minimal essential medium (α-MEM), Glasgow's minimal essential medium (GMEM), Iscove's modified Dulbecco's medium (IMDM), and combinations thereof.

* * * * *